(12) United States Patent
Bangert (10) Patent No.: US 9,091,688 B2
(45) Date of Patent: Jul. 28, 2015

(54) METHOD AND APPARATUS FOR THE DETECTION OF MAGNETIZABLE PARTICLES

(75) Inventor: Joachim Bangert, Erlangen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 1735 days.

(21) Appl. No.: 11/783,020

(22) Filed: Apr. 5, 2007

(65) Prior Publication Data

US 2008/0014651 A1 Jan. 17, 2008

(30) Foreign Application Priority Data

Apr. 6, 2006 (DE) .......................... 10 2006 016 334

(51) Int. Cl.
*G01N 27/87* (2006.01)
*G01N 33/543* (2006.01)

(52) U.S. Cl.
CPC .... *G01N 33/54326* (2013.01); *G01N 33/54353* (2013.01)

(58) Field of Classification Search
USPC ......... 365/173; 356/338; 436/86–90, 94, 149, 436/526; 324/214
See application file for complete search history.

(56) References Cited

U.S. PATENT DOCUMENTS

| | | | |
|---|---|---|---|
| 5,304,975 A * | 4/1994 | Saito et al. .................. 338/32 R |
| 5,514,452 A * | 5/1996 | Araki et al. ................ 428/811.2 |
| 5,981,297 A | 11/1999 | Baselt | |
| 6,468,809 B1 * | 10/2002 | Prinz et al. ..................... 436/526 |
| 6,510,031 B1 * | 1/2003 | Gambino et al. ............. 360/324 |
| 6,623,984 B1 * | 9/2003 | Fleischman et al. .......... 436/526 |
| 6,736,978 B1 * | 5/2004 | Porter et al. ................... 210/695 |
| 6,743,639 B1 | 6/2004 | Tondra et al. | |
| 7,106,051 B2 * | 9/2006 | Prins et al. ..................... 324/204 |
| 7,504,262 B2 * | 3/2009 | Fox ............................... 436/149 |
| 7,651,871 B2 * | 1/2010 | Sharma ......................... 436/526 |
| 7,682,838 B2 * | 3/2010 | Wang et al. ................... 436/526 |
| 7,729,093 B1 * | 6/2010 | Zhou ........................ 360/327.22 |
| 2002/0060565 A1 * | 5/2002 | Tondra .......................... 324/260 |

(Continued)

FOREIGN PATENT DOCUMENTS

DE        100 36 356 C2    3/2002
WO    WO 2005/111596 A1    11/2005

(Continued)

OTHER PUBLICATIONS

Edelstein et al . "The BARC biosensor applied to the detection of biological warfare agents." 2000. Biosensors and Bioelectronics. vol. 14, pp. 805-813.*

(Continued)

*Primary Examiner* — Arlen Soderquist
(74) *Attorney, Agent, or Firm* — Roberts Mlotkowski Safran & Cole, P.C.; David S. Safran (57) ABSTRACT

A method is disclosed for the detection of magnetic particles, so-called beads, immobilized on an essentially flat-planar holding area of a substrate. In at least one embodiment, a sensor array, which is arranged in the holding area and is composed of XMR sensors, is subjected to an external magnetic field and the change in the resistance of an XMR sensor caused by a stray field of a bead is measured to detect the bead, with the external field being produced by passing a direct current through a conductor track which is arranged on the holding area.

35 Claims, 6 Drawing Sheets

(56) References Cited

U.S. PATENT DOCUMENTS

| | | |
|---|---|---|
| 2002/0076825 A1* | 6/2002 | Cheng et al. .................. 436/174 |
| 2002/0191451 A1* | 12/2002 | Kishi et al. ................... 365/200 |
| 2004/0023365 A1 | 2/2004 | Engel et al. |
| 2004/0137275 A1* | 7/2004 | Jander et al. .................. 428/692 |
| 2004/0219695 A1* | 11/2004 | Fox ............................... 436/526 |
| 2004/0253744 A1* | 12/2004 | Rife et al. ..................... 436/514 |
| 2004/0259271 A1* | 12/2004 | Tondra .......................... 436/526 |
| 2005/0087000 A1* | 4/2005 | Coehoorn et al. ............ 73/53.01 |
| 2005/0100930 A1* | 5/2005 | Wang et al. ....................... 435/6 |
| 2005/0106758 A1* | 5/2005 | Fukumoto et al. ............ 436/526 |
| 2005/0244873 A1* | 11/2005 | Ikeda et al. ....................... 435/6 |
| 2006/0019373 A1* | 1/2006 | Kahlman et al. ........... 435/287.2 |
| 2006/0214658 A1* | 9/2006 | Kahlman ...................... 324/252 |
| 2006/0216836 A1* | 9/2006 | Pullini et al. .................... 438/3 |
| 2007/0063695 A1* | 3/2007 | Ruhrig ..................... 324/207.21 |
| 2007/0172890 A1* | 7/2007 | Prins et al. ..................... 435/7.1 |
| 2008/0032423 A1* | 2/2008 | Wang et al. ................... 436/536 |
| 2008/0206104 A1* | 8/2008 | Prins et al. ................. 422/82.01 |
| 2009/0224755 A1* | 9/2009 | Kahlman et al. .............. 324/252 |
| 2009/0243594 A1* | 10/2009 | Kahlman ....................... 324/202 |

FOREIGN PATENT DOCUMENTS

| | | | |
|---|---|---|---|
| WO | WO 2006/018811 A1 | | 2/2006 |
| WO | WO/2006/059270 | * | 6/2006 |
| WO | WO 2006/080558 A1 | | 8/2006 |

OTHER PUBLICATIONS

Lagae, L. et al, Journal of Applied Physics 2002, 91, 7445-7447.*

Graham, D. L. et al, Journal of Applied Physics 2002, 91, 7786-7788.*

Smith, C. H. et al, Sensors EXPO May 21, 2002, 11 pages.*

D.L. Graham [u.a.]: Single magnetic microsphere placement and detection on-chip using current line designs with integrated spin valve sensors: Biotechnological applications; Journal of Applied Physics (2002), vol. 91, Nr. 10, S. 7786-7788.

L. Lagae [u.a.]: On-chip manipulation and magnetization assessment of magnetic bead ensembles by integrated spin-valve sensors. Journal of Applied Physics (2002), vol. 91, Nr. 10, S. 7445-7447.

* cited by examiner

METHOD AND APPARATUS FOR THE DETECTION OF MAGNETIZABLE PARTICLES

The invention relates to a method for the detection of magnetic particles. The invention also relates to an apparatus for the detection of magnetic particles which are immobilized on a holding area of a substrate.

By way of example, magnetic particles are immobilized on a holding area of a substrate during the observation of biological processes and reactions in the field of pharmaceutical production and/or medical care, or when searching for the genetic code of cancer cells or viruses. If, for example, a search is being carried out for the presence of specific DNA sequences in tissues or body liquids, an analyte solution which contains these DNA sequences is, for example, applied to the holding area of a bio chip. Synthetic DNA sequences which are complementary to the DNA sequences being looked for are immobilized on the holding area. If there is an adequate match in the basic sequence, a hybridization reaction is carried out, that is to say bonding takes place between the DNA sequences that are being looked for and the complementary DNA sequences. Before or after the hybridization reaction, a magnetic particle, in the form of a magnetic bead, is fixed to the biotinated complement with the aid of a biotin-streptavidin coupling. Magnetic beads that have not been coupled are removed by rinsing.

The hybridization reactions that have taken place are read by detection of the magnetic beads. For this purpose, a magnetic field, referred to in the following text as an "external field", is applied to the holding area. In this case, as a reaction to the external field, the magnetic bead produces a locally limited stray field, that is to say a depolarizing field, which is detected with the aid of a suitable magneto-resistive sensor, in particular a so-called XMR sensor. In this case, the expression XMR sensors means in particular GMR (Giant Magnetic Resonance)—or TMR (Tunnel Magnetic Resonance) sensors.

In order to ensure that the XMR sensors are highly sensitive, it is necessary to exploit the external field as well as possible. If, for example, the external field is aligned parallel to the sensor sensitivity, tilting or maladjustment of an external field would produce bead reaction or stray field components which cannot be detected by the sensor. If the external field and the sensor sensitivity are aligned orthogonally, even a small amount of tilting would result in field components in the sensitivity direction which cannot easily be distinguished from a bead reaction. XMR sensors are formed from a plurality of material layers, for example from a first ferromagnetic layer with a fixed magnetization direction, a second ferromagnetic layer with a variable magnetization direction, that is to say its magnetization direction can be influenced by an external field, and an intermediate layer composed of a non-ferromagnetic material. The layers are aligned plane-parallel with respect to one another as a result of the use of lithographic processes for their production and the quality of the surfaces to which they are applied, in particular surfaces of substrates. The magnetization directions of the ferromagnetic layers run in the flat plane of the XMR sensor and in the layer planes.

The sensor sensitivity runs exactly on the layer plane or orthogonally to it. The variable layer is influenced to the greatest extent when the external field is aligned parallel to the layer plane. A corresponding situation applies to XMR sensors whose sensor sensitivity is oriented orthogonally to their flat plane. The external field is conventionally produced by a coil arrangement which, for example, is in the form of a Helmholtz coil pair and is fixed to the substrate by means of an auxiliary structure. In this case, some tilting of the external field with respect to the XMR sensor, that is to say a discrepancy in the parallel or orthogonal alignment of the external field and the sensor sensitivity, is virtually impossible to avoid despite considerable installation and adjustment effort. Furthermore, the magnetic field produced by a coil is intrinsically not exactly homogeneous, because of production-dependent geometric errors.

Arrangements of magnetic beads in which the beads are manipulated by means of external fields are known from the publications 'Journal of Applied Physics', Volume 91, No. 10, pages 7445-7447 and pages 7786-7788. In particular, nano-particles are used as magnetic particles for biotech applications. Furthermore, WO 2005/111596 A1 describes a corresponding measurement process in which an external field is produced by means of a conductor track ('current wire') which is arranged in the holding area of the substrate and through which an alternating current is passed.

Against this background, the object of the invention is to specify a method and to provide an apparatus that is suitable to carry out this method, by means of which the disadvantages mentioned above of excessively low sensitivity and/or instability resulting from inexact alignment of the XMR sensor can be avoided, or at least reduced.

The subject matter of the invention is an analysis method and an associated apparatus, by means of which magnetic measurement of the stray fields caused by magnetic markers is possible in a simple manner. The important factor in this case is that the field production for activation of the magnetic markers is combined with the current and, in particular, the field is generated by the sensor current itself. This compensates for the otherwise unavoidable errors resulting from the positioning of the XMR sensors with respect to the flat-plane holding area.

Thus, in the method according to the invention, the external field which excites the magnetic particles is advantageously produced by passing a direct current through a conductor track which is arranged on the holding area of the substrate. An apparatus according to the invention for production of an external field accordingly has an electrical conductor track which is arranged on the holding area and is connected to a direct-current source.

The latter refinements according to the invention avoid the error sources mentioned initially, specifically the alignment error of a coil arrangement and its production-dependent geometry errors. The conductor track mentioned may be applied together with an XMR sensor array to, for example, a flat-plane mounting surface on the substrate thus virtually precluding the possibility of mutual tilting. The external field which is formed around the conductor track when current flows advantageously extends exactly parallel to the said surface of the substrate and to the flat plane of the XMR sensor array. The parallel profile of the conductor track and sensor or sensor array can be achieved without major technical difficulties, in particular if one or more conductor tracks are applied together with an XMR sensor array to a common flat mount or else directly to the substrate, for example using methods that are known from chip technology.

In one particularly preferred method variant, an electrical direct current is passed through at least one electrically conductive layer of an XMR sensor in order to produce an external field. This variant completely precludes any alignment error between the external field and the sensor sensitivity, since the XMR sensor and the conductor track which produces an external field are either identical or form a physical unit. The electrically conductive layer may be part of the XMR sensor or may be a separate layer which does not contribute to the sensor function. In an entirely general form a direct current is passed through an XMR sensor in order to determine the change in the resistance of the XMR sensor caused by a stray field. In one preferred variant, this measure is at the same time used to produce the external field, in that a current level is applied to the XMR sensor which is sufficient to produce an external field which extends into the area in which a bead that is immobilized on the holding area is located. This means that virtually no more special devices whatsoever are required to produce an external field.

The proposed method allows a large number of widely differing design variants for XMR sensor arrays. For example, it is possible to use XMR sensors with a sensor sensitivity oriented parallel to their flat plane, with the beads being immobilized on the upper face, that is to say the side of an XMR sensor facing away from the substrate, because the external field which surrounds the XMR sensor there runs essentially on the flat plane of the sensor. In contrast, when using XMR sensors whose sensor sensitivity is oriented orthogonally with respect to their flat plane, the beads are immobilized on a part of the holding area which flanks the XMR sensor and to which the external field is applied. This arrangement is based on the idea that the stray field which originates from a bead has predominantly orthogonal field components, which can therefore be detected by the XMR sensor, in its side areas, that is to say the areas facing the XMR sensor. In one particularly advantageous arrangement, the sensor sensitivity is increased by using two adjacent XMR sensors to produce two external fields which overlap in an area between the sensors and form an overlap zone with an increased field strength, with beads being immobilized in a part of the holding area to which the overlap zone is applied, and using XMR sensors whose sensor sensitivity is oriented orthogonally with respect to their flat plane. The field is naturally increased in the overlap area only when current passes through the adjacent XMR sensors in opposite senses. In a similar method variant, an XMR sensor whose sensor sensitivity is oriented orthogonally with respect to its flat plane is arranged on that part of the holding area which flanks a conductor track, with beads being immobilized on its upper face. Two adjacent conductor tracks with opposite polarity are preferably used to produce two overlapping external fields, with beads being immobilized on the upper face of an XMR sensor which is arranged in the overlap area.

In the case of XMR sensors which are formed only from electrically conductive layers, current flows essentially along the layers of these sensors during a resistance measurement. This situation differs from that in the case of TMR sensors which, in addition to electrically conductive outer layers, have at least one electrically insulating intermediate layer which acts as a tunnel barrier, with current flowing transversely through the layers of the sensors during a resistance measurement. The stacked arrangement of the said layers results in the current being diverted transversely with respect to the layer planes, so that no external field that is adequate for the purpose under discussion is created in the desired direction. For sensors such as these, one method variant provides for a direct current to be passed through a first outer layer in order to produce an external field, with the direct current being independent of any TMR sensor current flow that is used to measure a resistance change. A TMR sensor is preferably used whose sensor sensitivity is oriented parallel with respect to its flat plane, with beads being immobilized on the upper face of the first outer layer.

In one preferred refinement of the apparatus, at least some of the XMR sensors are in the form of strips or lines. The sensors may in this case be of such a size that only one or only a small number of magnetic markers can be located over the width, with this being the case in the event of a width of about 1 μm to 20 μm, and in particular of 2 μm to 8 μm. The magnetic markers are in this case so-called magnetic beads, which are available in a suitable size.

The latter refinement of the invention is based on the idea that the resistance effect caused by beads being located in the sensor is at its greatest when as many beads as possible, and resistance changes caused by them in the XMR sensor, are arranged in the sense of resistances connected in series. In contrast, beads which are arranged alongside one another in the width direction of the sensor act like parallel-connected resistors, that is to say they exert only a minor effect on the XMR sensor. Linear alignment of the sensors is preferable, for example with a parallel arrangement. However, other arrangements of the sensors are also feasible, for example in the form of concentric circles or spirals.

In a further preferred refinement, the XMR sensors for detection of stray fields are in the form of TMR sensors having a first and a second electrically conductive outer layer and having at least one electrically insulating intermediate layer which forms a tunnel barrier, with a first outer layer forming a conductor track and being connected into a direct-current circuit, which is separate from an evaluation circuit that is used for resistance measurement. The separation ensures that the evaluation circuit is independent of the direct-current circuit that is used to produce the external field, and can be designed in the form of a direct-current or alternating-current circuit.

In the case of an apparatus which is equipped with TMR sensors, it is advantageous for a first outer layer, which is in the form of a strip or strips or a line or lines, to be connected to a plurality of intermediate layers and second outer layers which are each isolated from one another. In this case, beads are immobilized on the upper face of the outer layer, to be precise in each case in the area of an intermediate layer. One development of this refinement provides for a plurality of first and second outer layers to be provided, which are each in the form of a strip or strips or line or lines and run parallel to one another, with the first outer layers crossing the second outer layers, and with an intermediate layer being provided at each of the crossing points. In this case, beads are immobilized at each of the crossing points, to be precise on the first outer layer, that is to say the outer layer which is used to produce an external field.

Further advantages and details of the invention will become evident from the description of the figures of exemplary embodiments, on the basis of the drawing and in conjunction with the patent claims.

In the figures.

Identical units have the same reference symbols in the figures. The examples in the individual figures are in some cases described jointly.

Figure 1:
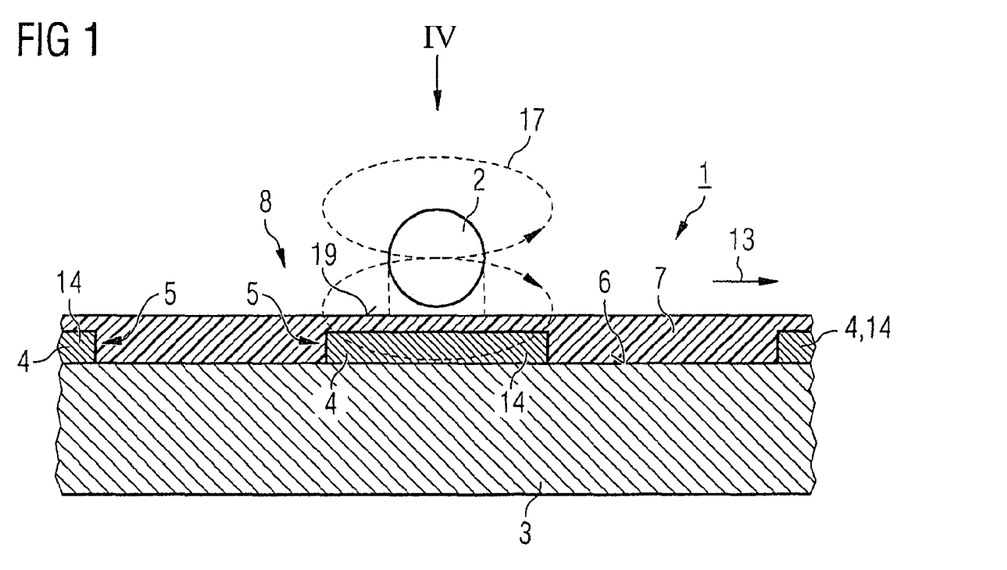
FIG. 1 shows an apparatus for detection of magnetic particles, comprising a substrate and a sensor array arranged on it.

The apparatus 1 shown in FIG. 1 for detection of beads 2 has a substrate 3 and a sensor array 5 formed from a plurality of XMR sensors 4. The substrate 3 has a flat planar mounting surface 6 on which XMR sensors 4 are fixed. A protective layer 7 is also applied to the mounting surface 6, and the sensor array 5 is embedded in it. The protective layer 7 is used for electrical isolation and for shielding from environmental influences. In addition, it is designed such that it can be used as a holding area 8 and is suitable for immobilization of biomolecules, in particular of DNA strands. However, a protective layer 7 is not absolutely essential. The area which contains sensor arrays 5 on the substrate 3 or the mounting surface 6 forms a holding area 8 for beads 2, although, as will be explained further below, these can be fixed or immobilized on different subareas of the holding area 8.

Figure 2:
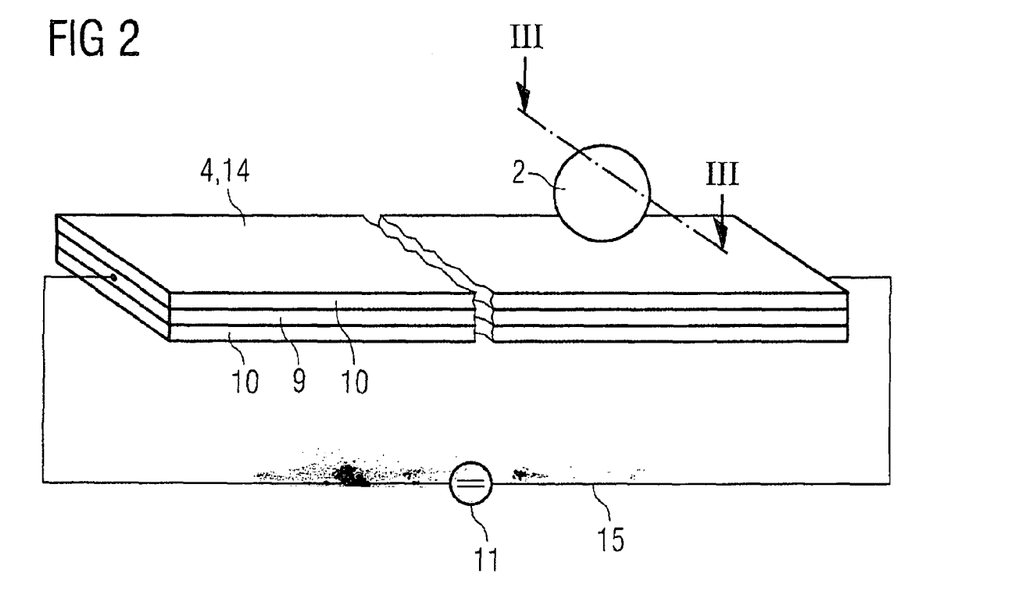
FIG. 2 shows a detail of the sensor array from FIG. 1, in the form of a schematic, perspective illustration.

By way of example, the apparatus shown in FIG. 2 uses GMR sensors which, for example, have a non-ferromagnetic electrically conductive intermediate layer 9 composed of copper, ruthenium, osmium or the like, with the intermediate layer 9 being between two ferromagnetic layers 10 composed, for example, of NiFe. A ferromagnetic layer 10 has a fixed magnetization direction, and the other layer has a magnetization direction which can be influenced by an external magnetic field or external field 13. In order to allow detection of beads 2, an external field 13 must be applied to the holding area 8.

Figure 3:
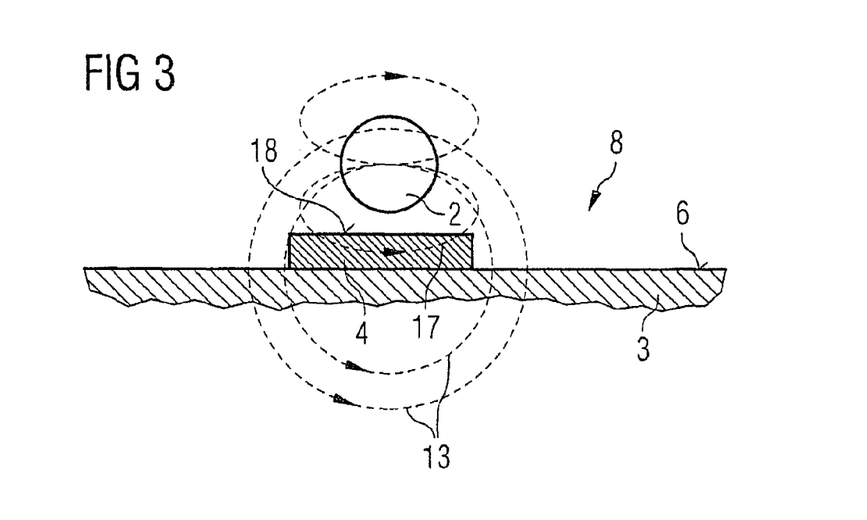
FIG. 3 shows a schematic section along the line III-III in FIG. 2.

As shown in FIG. 3, the external field 13 is now not produced by a coil arrangement that is fixed to the apparatus 1 by means of an auxiliary structure, but by at least one conductor track 14 arranged in the holding area 8. The conductor track 14 is in this case connected to a direct-current source 11, as part of a direct-current circuit 15.

The current flow through the XMR sensor is thus used on the one hand for resistance measurement and on the other hand for production of the external field 13 in FIG. 3. The current level is chosen such that the conductor track 14 through which the current flows produces an external field 13 such as this, which extends into the area in which a bead 2 is located. A bead 2 has a size, for example, of 1-2 μm and is composed, for example, of a styrene matrix, in which ferromagnetic particles are incorporated.

The XMR sensors 4 may advantageously be in the form of strips or lines, having a width, for example, of 5 μm. In order to ensure that the stray field 17, that is to say the field which produces a measurable resistance change in the XMR sensor, at the location of a bead 2 is sufficiently strong, a current of 10 mA is required, for example, for a GMR sensor with a width of 5 μm. This produces an external field of 1 kA/m at a distance of about 200 nm above the sensor surface. In the case of the exemplary embodiment shown in FIGS. 1 to 3, a bead 2 is immobilized on the upper face 18 of the XMR sensor or, as is illustrated in FIG. 1, on the upper face 19 of the protective layer 7 which covers the XMR sensor 4.

The external field 13 which surrounds the XMR sensor 4, to be precise the conductor track 14 formed by it, is illustrated in a simplified form in FIG. 3. That area of the external field 13 which passes through a bead 2 arranged on the upper face 18 of the XMR sensor 4 is aligned essentially parallel to the flat plane of the XMR sensor 4. The stray field 17 which is formed at the location of the bead 2, and is likewise illustrated in a simplified form, passes through the XMR sensor 4 aligned essentially parallel to its flat plane. The sensor sensitivity of the XMR sensor 4 is oriented parallel to its flat plane. The XMR sensors 4 are aligned linearly and parallel to one another, separated by a lateral distance. However, other forms are also conceivable. For example, XMR sensors may be provided on the mounting surface 6 in the form of concentric circles or in the form of spirals.

Figure 4:
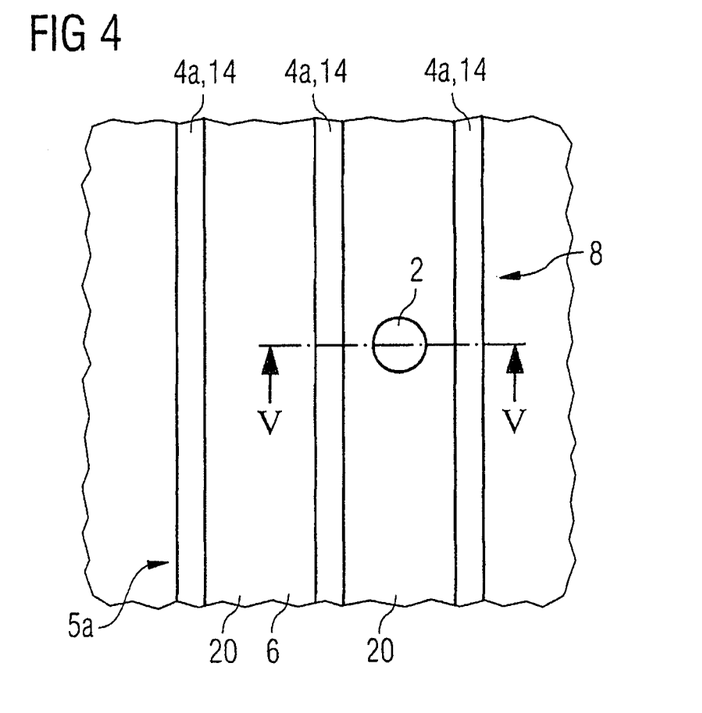
FIG. 4 shows a plan view in the direction of the arrow IV in FIG. 1 of an apparatus, but with an alternatively designed sensor array being provided.
Figure 5:
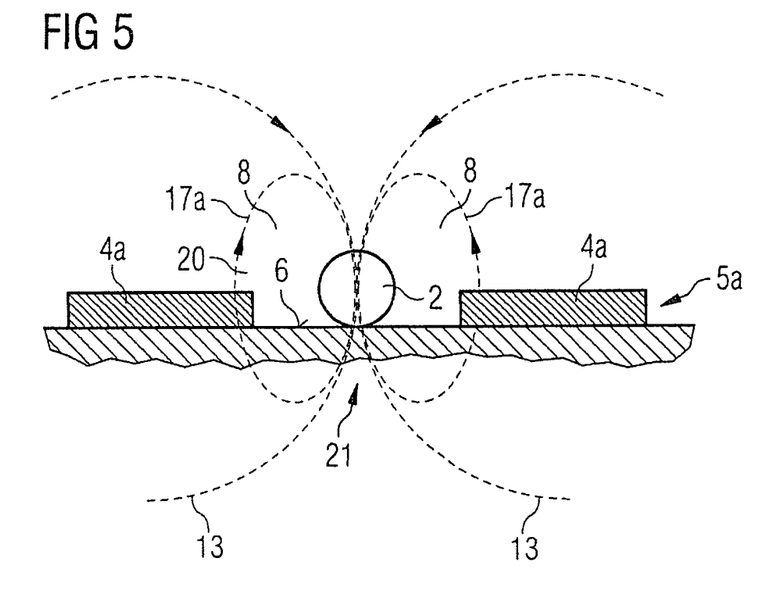
FIG. 5 shows a schematic section illustration along the line IV-IV in FIG. 4.

FIG. 4 and FIG. 5 show a sensor array 5a in which XMR sensors 4a whose sensor sensitivity is oriented orthogonally with respect to their flat plane are used. The XMR sensors 4a are in the form of strips and are fitted to the mounting surface 6 of the substrate such that they are arranged parallel, but with a lateral distance between them. Adjacent XMR sensors 4a have opposite polarity and are laterally separated from one another by a sufficient distance that their external fields 13 overlap in a part 20 of the holding area 8 that is located between the XMR sensors 4a. In this case, the overlap area 21, which is located between the XMR sensors 4a, of the external fields 13 is provided for immobilization of beads 2. The stray field 17a caused by the bead 2 extends with its lateral outer areas into the XMR sensors 4a, and passes through them, aligned essentially orthogonally. This leads to a resistance change in the XMR sensors 4a whose sensitivity is oriented orthogonally with respect to their flat plane.

Figure 6:
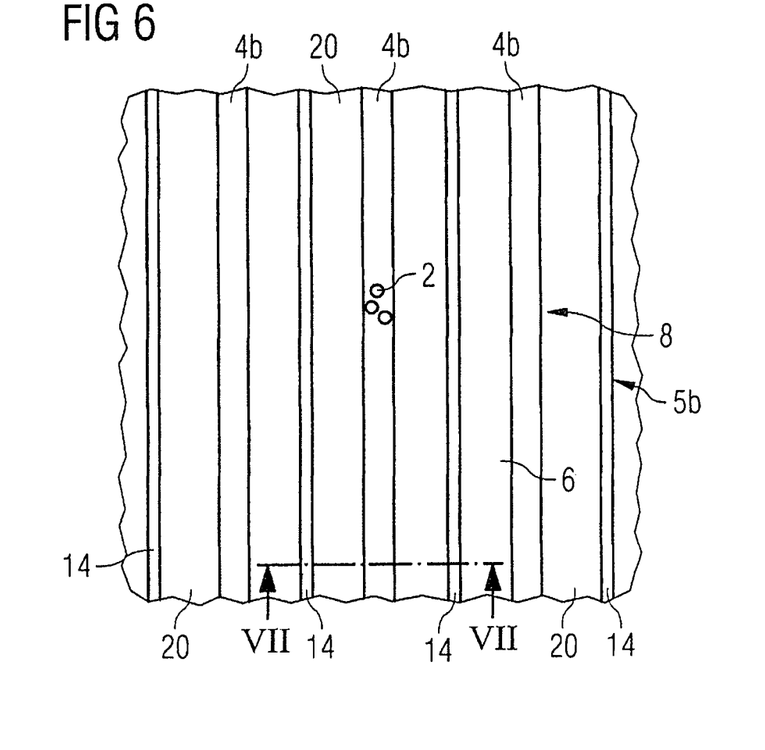
FIG. 6 shows a view, corresponding to that in FIG. 4, of a refinement of the sensor array that has been modified in comparison to that shown in FIG. 4.
Figure 7:
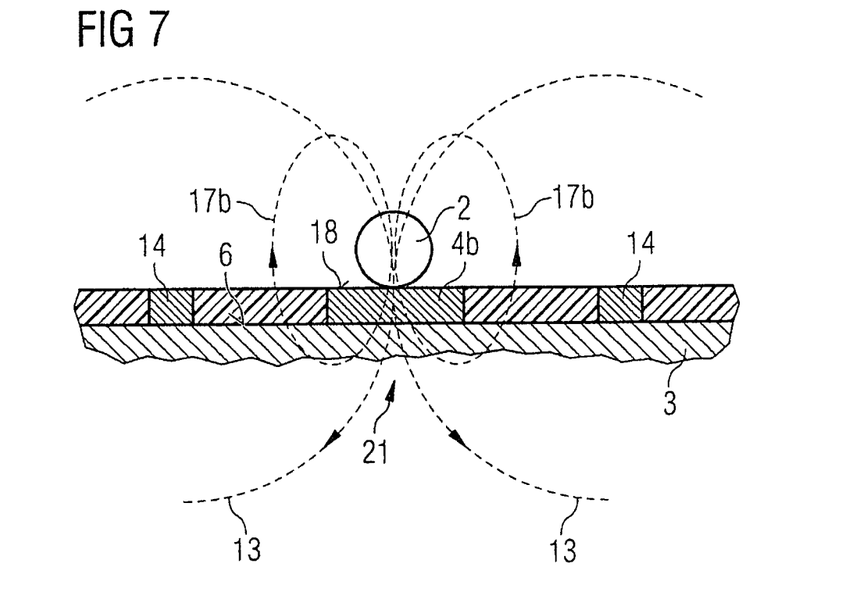
FIG. 7 shows a schematic cross section along the line VII-VII in FIG. 6.

FIG. 6 and FIG. 7 show an exemplary embodiment in which XMR sensors 4b whose sensor sensitivity is likewise orthogonal are admittedly likewise provided. However, separate electrical conductor tracks 14 are applied to the mounting surface 6 in order to produce external fields 13. The conductor tracks 14 run in straight lines and parallel to one another, and are separated so far from one another that the external fields 13 of two adjacent conductor tracks 14 with opposite polarity overlap in an overlap area 21 located between them. An XMR sensor 4b whose sensor sensitivity is oriented orthogonally is arranged in this area, in which the overlapping external fields 13 are aligned orthogonally with respect to the mounting surface 6 of the substrate 3, and with respect to the flat plane of the sensor array 5b. As in the case of the previous exemplary embodiment as well, the magnetic field in the overlap area 21 is stronger than the individual external fields 13. The resultant stray field 17b and the resistance change in the XMR sensors 4b are accordingly stronger. In the present exemplary embodiment as well as in the other exemplary embodiments, it is possible, for example, to use sensors as known from DE 100 36 356 C2 as sensors with orthogonal sensor sensitivity.

The XMR sensors, which have been described on the basis of the previous examples and are at the same time used as conductor tracks 14 to produce an external field 13, are formed exclusively from electrically conductive layers. In contrast, TMR sensors have at least one electrically insulating layer, which is used as a tunnel barrier, and, in the simplest version, these are enclosed between two electrically conductive outer layers. In the case of a sensor such as this, the current does not flow longitudinally with respect to its layers, but transversely with respect to them, in order to measure the resistance. As has already been mentioned further above, this current cannot be increased sufficiently to allow an adequate external field to be produced. As can be seen from the outline illustration in FIG. 8, a separate current, which is used exclusively to produce the external field, is passed through an outer layer 22 of an XMR sensor for this purpose. For this purpose, the outer layer 22 as part of a direct-current circuit 25 is connected to a direct-current source 11, with the direct-current circuit 25 being electrically isolated from an evaluation circuit 27 which is used for resistance measurement.

The electrical isolation allows the evaluation circuit to be designed independently of the direct-current circuit 25, in particular in terms of current level and signal form, that is to say direct current, alternating current or current pulses.

Figure 8:
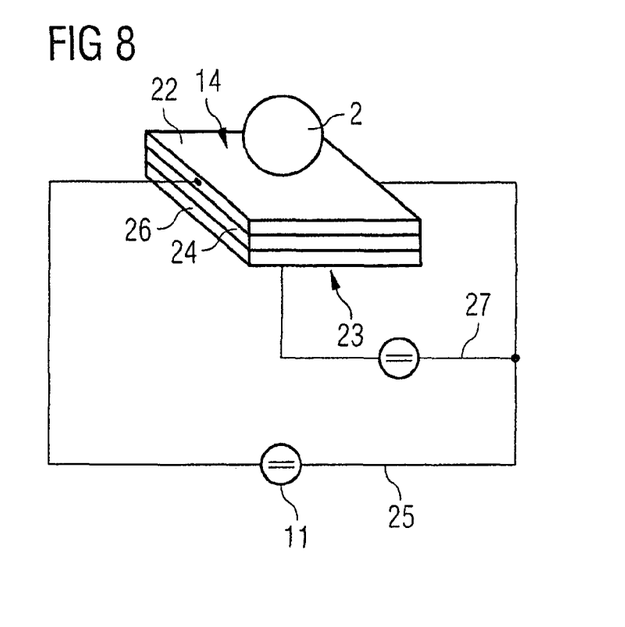
FIG. 8 shows a schematic perspective illustration of a TMR sensor.

The external field which surrounds the outer layer that forms a conductor track 14, but which is not illustrated in detail in FIG. 8, is approximately in the same form as in the case of the exemplary embodiments described above, and accordingly runs on the upper face 18 of the TMR sensor 23, essentially parallel to its flat plane. The sensor must therefore have a sensitivity which is oriented parallel to its flat plane.

A sensor array can be formed from a multiplicity of the sensors illustrated in FIG. 8. However, in order to increase the sensor sensitivity, refinements in the form of strips or lines are preferred. In the exemplary embodiment shown in FIG. 9, a plurality of TMR sensors 23a, 23b which are arranged in a row and at a distance from one another have a common outer layer 22a, which is in the form of a strip or strips. A plurality of intermediate layers 24, which are used as, a tunnel barrier, and outer layers 26 are applied to the lower face of the outer layer 22, facing the substrate, although this is not illustrated in detail in FIG. 9. The outer layer 22 is connected into a direct-current circuit 25a in order to produce an external field 13, which is not indicated separately in FIG. 8. An external field which is formed when current passes through the outer layer 22 is aligned essentially parallel to the outer layer 22, in the area of its upper face 18.

Figure 9:
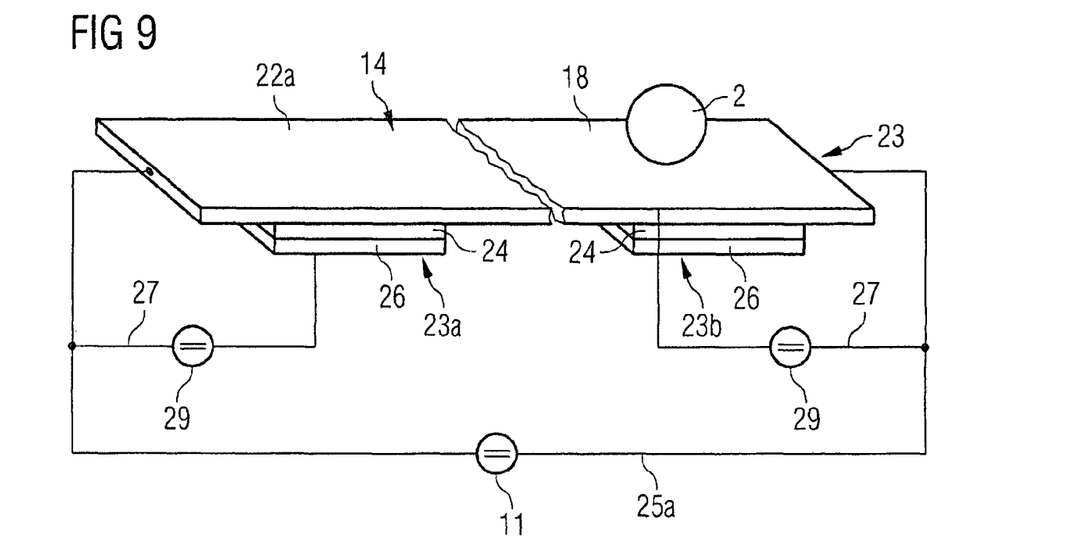
FIG. 9 shows a schematic perspective detail of a sensor array formed from TMR sensors.

A stray field which is caused by the presence of a bead 2, but is not indicated separately in FIG. 8, is likewise aligned essentially parallel to the outer layer 22 on the side of the bead 2 pointing toward a TMR sensor 23a, 23b. XMR sensors whose sensor sensitivity is oriented parallel to their flat plane can therefore be used for the refinement of a sensor array that is significant in this case. For resistance measurement purposes, each TMR sensor 23a, 23b is connected into an evaluation circuit 27, which is in the form of a direct-current circuit, and is connected to a direct-current source 29. As shown in FIG. 9, a plurality of TMR sensors 23 can be arranged parallel alongside one another in order to form a sensor array.

Figure 10:
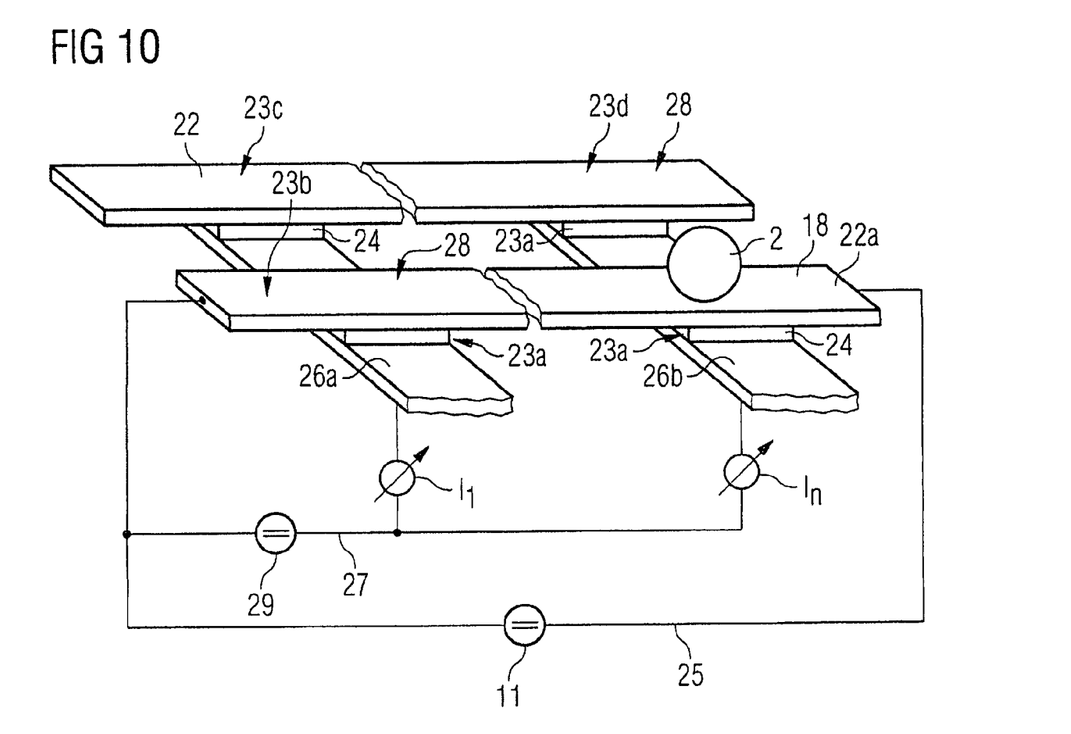
FIG. 10 shows a schematic perspective view of a sensor array which has been modified from that shown in FIG. 9.

In the exemplary embodiment shown in FIG. 10, the second outer layers 26a are also enlarged, as well as the outer layers 22, specifically being lengthened in the form of strips or lines. The outer layers 22, which are arranged parallel and with a lateral distance between them, cross the outer layers 26a, 26b, which are likewise arranged parallel and with a lateral distance between them. The outer layers are each separated from one another at the crossing points 28, by means of an intermediate layer 24 which is used as a tunnel barrier. As is shown in FIG. 9 for the outer layer 22a, the outer layers 22 are part of a direct-current circuit 25. When current flows, an external field is formed which surrounds the outer layers 22, although this is not indicated separately in FIG. 9.

The crossing points 28 act as locations for immobilization of beads 2. The external field of the outer layer 22 extends into the area in which a bead 2 is located. The stray field caused by a bead 2, which is not shown in FIG. 9, causes a resistance change in the area of the individual sensors 23a-d formed at the crossing points 28. In this case as well, TMR sensors with a parallel sensor sensitivity are required for bead detection. As is shown in FIG. 9 for the crossing points 28a, 28b, the crossing points 28 have a current $I_1$ or $I_n$ applied to them for resistance measurement.

The invention claimed is:

1. A method for detecting magnetic particles immobilized on an essentially flat-planar holding area of a substrate, the method comprising:
    creating an external magnetic field for detecting magnetic particles by passing a direct current through at least one electrically conductive layer of an XMR sensor of an XMR sensor array, said XMR sensor array being located on a surface of a substrate;
    subjecting the XMR sensor array to the external magnetic field, wherein:
        the XMR sensor array is arranged in the holding area,
        the XMR sensor array includes a plurality of XMR sensors,
        the XMR sensors, comprises a non-ferromagnetic layer between two ferromagnetic layers; and
    measuring a resistance change of the at least one XMR sensor caused by a stray field produced from the magnetic particles due to the external magnetic field to detect the magnetic particles.

2. The method as claimed in claim 1, wherein the magnetic particles are magnetic beads.

3. The method as claimed in claim 2, wherein a current level of the direct current that produces the external magnetic field extends into an area in which a bead of the magnetic beads is located, and is applied to the XMR sensor array to determine the resistance change of the at least one XMIR sensor.

4. The method as claimed in claim 3, wherein the at least one XMR sensor has a sensor sensitivity oriented parallel to a flat plane of the at least one XMR sensor, and the beads are immobilized on an upper face of the XMR sensor.

5. The method as claimed in claim 3, wherein the at least one XMR sensor has a sensor sensitivity oriented orthogonally with respect to a flat plane of the at least one XMR sensor, and the beads are immobilized in a part of the holding area which flanks the that at least one XMR sensor.

6. The method as claimed in claim 5, wherein two mutually overlapping external fields are produced with the aid of two adjacent oppositely polarized XMR sensors of the plurality of XMR sensors, with the beads being immobilized in a part of the holding area to which the overlap zone is applied, and with the two XMR sensors having sensor sensitivities oriented orthogonally with respect to a flat plane of the two XMR sensors.

7. The method as claimed in claim 2, wherein the at least one XMR sensor has a sensor sensitivity oriented orthogonally with respect to a flat plane of the at least one XMR sensor, and is arranged in a part of the holding area which flanks the conductor track, and wherein the beads on an upper face of the at least one XMR sensor are immobilized.

8. The method as claimed in claim 7, wherein two overlapping external fields are produced with the aid of two adjacent oppositely polarized conductor tracks, with the beads being immobilized on an upper face of an XMR sensor of the plurality of XMR sensors arranged in the overlap area.

9. The method as claimed in claim 1, wherein a TMR sensor, having a first and a second electrically conductive outer layer and having an electrically insulating intermediate layer used as a tunnel barrier, is used as the at least one XMR sensor, and wherein the direct current is passed through the first outer layer to produce the external magnetic field is independent of a current which is passed through the TMR sensor in order to measure the resistance change.

10. The method as claimed in claim 9, wherein the TMR sensor has a sensor sensitivity oriented parallel to a flat plane of the TMR sensor, and the beads on an upper face of the first outer layer are immobilized.

11. The method of claim 1, wherein the measuring of the resistance change is used to detect the magnetic particles.

12. The method of claim 1, wherein:
the conductor track generates the external magnetic field;
the external field is not produced by a coil arrangement; and
the external field extends exactly parallel to the surface of the substrate and the flat plane of the XMR sensor array.

13. An apparatus for detection of magnetic particles in the form of beads, comprising:
a holding area arranged on a surface of a substrate, wherein:
the holding is configured to immobilize the beads, and
the holding area includes at least one sensor array formed from a plurality of XMR sensors; and
an external magnetic field producing device is arranged on a surface of the substrate in the holding area, wherein:
the external magnetic field producing device causes a stray field in the beads for detection of the beads,
the external magnetic field producing device includes a direct-current source and an electrical conductor track,
the electrical conductor track is on a surface of the substrate,
the electrical conductor track includes at least one electrically conductive layer of at least one XMR sensor of the sensor array, and
the XMR sensor comprises a non-ferromagnetic layer between two ferromagnetic layers and is connected to the direct-current source.

14. The apparatus as claimed in claim 13, wherein at least some of the plurality of XMR sensors are in the form of at least one of strips and lines.

15. The apparatus as claimed in claim 14, wherein the at least some of the plurality of XMR sensors are aligned parallel, at a distance alongside one another.

16. The apparatus as claimed in claim 15, wherein at least one XMR sensor includes a sensor sensitivity oriented parallel to a flat plane of the least one XMR sensor, with an upper face of the at least one XMR sensor being used to immobilize beads.

17. The apparatus as claimed in claim 15, wherein at least one XMR sensor includes a sensor sensitivity oriented orthogonally with respect to a flat plane of the least one XMR sensor, with a part of the holding area which flanks the at least one XMR sensor being used for immobilization of the beads.

18. The apparatus as claimed in claim 14, wherein at least one XMR sensor includes a sensor sensitivity oriented parallel to a flat plane of the least one XMR sensor, with an upper face of the at least one XMR sensor being used to immobilize beads.

19. The apparatus as claimed in claim 14, wherein at least one XMR sensor includes a sensor sensitivity oriented orthogonally with respect to a flat plane of the least one XMR sensor, with a part of the holding area which flanks the at least one XMR sensor being used for immobilization of the beads.

20. The apparatus as claimed in claim 13, wherein at least one XMR sensor of the plurality of XMR sensors includes a sensor sensitivity oriented parallel to a flat plane of the at least one XMR sensor, with an upper face of the at least one XMR sensor being used to immobilize beads.

21. The apparatus as claimed in claim 13, wherein at least one XMR sensor of the plurality of XMR sensors includes a sensor sensitivity oriented orthogonally with respect to a flat plane of the at least one XMR sensor, with a part of the holding area which flanks the at least one XMR sensor being used for immobilization of the beads.

22. The apparatus as claimed in claim 21, wherein two XMR sensors of the plurality of XMR sensors, which are adjacent but separated laterally and include mutually opposite polarity, are connected to the direct-current source, with a part of the holding area between the two XMR sensors being used for immobilization of the beads.

23. The apparatus as claimed in claim 13, wherein an XMR sensor of said plurality of XMR sensors has a sensor sensitivity is oriented orthogonally with respect to a flat plane of the XMR sensor and is arranged in a part of the holding area which flanks the conductor track.

24. The apparatus as claimed in claim 23, wherein the XMR sensor is flanked by two conductor tracks with mutually opposite polarity.

25. The apparatus as claimed in claim 13, wherein at least one TMR sensor including a first and a second electrically conductive outer layer and including at least one electrically insulating intermediate layer, which forms a tunnel barrier, is provided for detection of the stray field, with a first outer layer forming a conductor track and being connected into a direct-current circuit which is separate from an evaluation circuit, used for measuring the resistance of the TMR sensor.

26. The apparatus as claimed in claim 25, wherein the evaluation circuit is a direct-current circuit.

27. The apparatus as claimed in claim 25, wherein the evaluation circuit is an alternating-current circuit.

28. The apparatus as claimed in claim 25, wherein a plurality of intermediate layers and second outer layers are connected to the first outer layer, in the form of at least one of at least one strip and at least one line.

29. The apparatus as claimed in claim 25, wherein a plurality of first and second outer layers, each in the form of at least one of a strip and a line and run parallel to one another, are provided, wherein the first outer layers cross the second outer layers, and wherein an intermediate layer is provided at each of the crossing points.

30. The apparatus as claimed in claim 13, wherein at least one of an XMR sensor of the plurality of XMR sensors and an outer layer of a TMR sensor has a width ranging from 1 μm to 20 μm.

31. The apparatus as claimed in claim 30, wherein the width is in a range from 2 μm to 8 μm.

32. The apparatus as claimed in claim 13, wherein the apparatus is in the form of a bio chip.

33. A bio chip comprising the apparatus as claimed in claim 13.

34. The apparatus of claim 13, wherein:
the conductor track generates the external magnetic field;
the external field is not produced by a coil arrangement; and
the external field extends exactly parallel to the surface of the substrate and the flat plane of the XMR sensor array.

35. A method for detecting magnetic particles immobilized on an essentially flat-planar holding area of a substrate, the method comprising:
passing a direct current through an XMR sensor in order to produce an external field for detecting magnetic particles, wherein the external field causes a stray field produced from the magnetic particles, and
determining the change in resistance of the XMR sensor caused by the stray field, wherein the same direct current flow is used for resistance measurement and for production of the external field.

* * * * *